United States Patent [19]
Cantor et al.

[11] Patent Number: 5,482,836
[45] Date of Patent: Jan. 9, 1996

[54] DNA PURIFICATION BY TRIPLEX-AFFINITY CAPTURE AND AFFINITY CAPTURE ELECTROPHORESIS

[75] Inventors: Charles R. Cantor, Boston, Mass.; Takashi Ito, Chiba, Japan; Cassandra L. Smith, Boston, Mass.

[73] Assignee: The Regents of the University of California, Oakland, Calif.

[21] Appl. No.: 4,552

[22] Filed: Jan. 14, 1993

[51] Int. Cl.$^6$ .............................. C12Q 1/68; C12P 19/34; C07H 17/00; C12N 15/00
[52] U.S. Cl. ................ 435/6; 435/91.1; 536/23.1; 536/24.3; 536/24.33; 536/25.3; 536/25.32; 935/1; 935/2; 935/4; 935/16; 935/19; 935/76; 935/77
[58] Field of Search ............... 435/6, 81.1; 536/23.1, 536/24.3, 24.33, 25.3, 25.32; 935/1, 2, 4, 16, 19, 76, 77

[56] References Cited

U.S. PATENT DOCUMENTS 5,176,996 1/1993 Hogan et al. ........................... 435/6
5,422,251 6/1995 Fresco, Jr. .

OTHER PUBLICATIONS

Moseraud Dervan, *Science*, vol. 238, 30 Oct. 1987, pp. 645–650.

Durland, et al., *Biochemistry*, 1991, 30, 9746–9255.

Kandpal, et al., *Nucleic Acids Research*, vol. 18, No. 7, 1990, pp. 1789–1795.

Lehninger, A. L., *Biochemistry*, 2nd edition, The Molecular Basis of Self Structure and Function, Worth Publishers, Inc. (1981) 9cover pages and p. 873).

Alberts, B. et al., *Molecular Biology of the Cell*, Garland Publishing, Inc.: New York (1983) (cover pages and p. 189).

Watson, J. D. et al., *Molecular Biology of the Gene*, 4th Edition, Benjamin/Cummings Publishing, Inc., Menlo Park, CA (1987) (cover pages and p. 44).

Sambrook, J. et l., *Molecular Cloning: A Laboratory Manual*, 2d edition, Cold Spring Harbor Press, Plainview, NY (1989) (cover pages and pp. 4.43, 5.78, 5.79, 6.20–6.23 and 8.64).

Ausubel, F. M. et al., *Short Protocols in Molecular Biology*, 2d edition, John Wiley & Sons, Inc., New York, NY (1992), coverpages and pp. 2.24–2.30.

Ranhand, J. M., The Enrichment of Plasmid DNAs, in Bacterial Cell Lysates, Using an Alakaline–pH Procedure That Does Not Permanently Denature Them, *Prep. Biochem* 15(3):121–131 (1985).

Drozhdenyuk, A. P. et al., Degradation of DNA in Standard Alkaline or Thermal Denaturation, *Biokhimiya* 41:1255 (1976).

Russeu, G. et al., Distribution of Histones in Alkali–Denatured Chromatin Studied by Isopycnic Centrifugation in Alkaline Metrizamide Density, *Nucleic Acids Res. (England)* 3:697–707 (1976).

(List continued on next page.)

Primary Examiner—W. Gary Jones
Assistant Examiner—Bradley L. Sisson
Attorney, Agent, or Firm—Flehr, Hohbach, Test, Albritton & Herbert

[57] ABSTRACT

The invention provides a method for purifying or isolating double stranded DNA intact using triple helix formation. The method includes the steps of complexing an oligonucleotide and double stranded DNA to generate a triple helix and immobilization of the triple helix on a solid phase by means of a molecular recognition system such as avidin/biotin. The purified DNA is then recovered intact by treating the solid phase with a reagent that breaks the bonds between the oligonucleotide and the intact double stranded DNA while not affecting the Watson-Crick base pairs of the double helix. The present invention also provides a method for purifying or isolating double stranded DNA intact by complexing the double stranded DNA with a specific binding partner and recovering the complex during electrophoresis by immobilizing it on a solid phase trap imbedded in an electrophoretic gel.

27 Claims, 5 Drawing Sheets

OTHER PUBLICATIONS

Eshaghpour, H. et al., Preparative Separation of the Complementary Stranmds of DNA Restriction Fragments by Alkaline, *Nucleic Acids Research* 5:13–21 (1978).

Koury, M. J. et al., "Erythropoietin Retards DNA Breakdown and Prevents Programmed Death in Erythroid Progenitor Cells", *Science,* 248:378–381 (1990).

Duncan, C. H. et al., "Mechanism of integrating foreign DNA during transformation of *Bacillus subtilus*", *Proc. Natl. Acad. Sci. USA,* 75:3664–3668 (1978).

Fischer, S. G. et al., "Separation of random fragments of DNA according to Properties of their sequences", *Proc. natl. Acad. Sci. USA,* 77:4420–4424 (1980).

Wells, R. D. et al. (1988), "The chemistry and biology of unusual DNA structures adopted by oligopurine•oligopyrimidine sequences", *FASEB J.* 2:2939–2949.

LeDoan, T. et al. (1987), "Sequence–specific recognition, photocrosslinking and cleavage of the DNA double helix by an oligo–[a]–thymidylate covalently linked to an azidoproflavine derivative", *Nucleic Acids Res.* 15:7749–7760.

Strobel, S. A. et al. (1991), "Single–site enzymatic cleavage of yeast genomic DNA mediated by triple helix formation", *Nature (London)* 350:172–174.

Koob, M. et al. (1990), "Cleaving Yeast and *Escherichia coli* Genomes at a Single Site", *Science* 250:271–273.

Lyamichev, V. I. et al. (1988), "A stable complex between homopyrimidine oligomers and the homologous regions of duplex DNAs", *Nucleic Acids Res.* 16:2165–2178.

Tsurui, H. et al. (1990), "A rapid and efficient cloning method with a solid–phase DNA probe: applicationfor cloning the 5'–flanking region of the gene encoding human fibronectin", *Gene* 88:233–239.

Griffen, L. C. et al. (1989), "Recognition of Thymine•Adenine Base Pairs by Guanine in a Pyrimidine Triple Helix Motif", *Science* 245:967–971.

Belotserkovskil, B. P. et al. (1990), "Formation of intramolecular triplex in homopurine–Homopyrimidine mirror repeats with point substitutions", *Nucleic Acids Res.* 18:6621–6624.

Horne, D. A. et al. (1990), "Recognition of Mixed–Sequence Duplex DNA by Alternate–Strand Triple–Helix Formation", *J. Am. Chem. Soc.* 112:2435–2438.

Cooney, M. et al. (1988), "Site–Specific Oligonucleotide Binding Represses Transcription of the Human c–myc Gene in Vitro", *Science* 241:456–459.

Kohwi, Y. et al. (1988), "Magnesium ion–dependent triple–helix structure formed by homopurine–homopyrimidine sequences in supercoiled plasmid DNA", *Proc. Natl. Acad. Sci. USA* 85:3781–3785.

Letai, A. G. et al. (1988), "Specificity in Formation of Triple–Stranded Nucleic Acid Helical Complexes: Studies with Agarose–Linked Polyribonucleotide Affinity Columns", *Biochemistry* 27:9108–9112.

Bernués J. et al. (1989), "Structuralpolymorphism of homopurine–homopyrimidine sequences: the secondary DNA structure adopted by a $d(GA \cdot CT)_{22}$ sequence in the presence of zinc ions", *EMBO J.* 8:2087–2094.

Beal, P. B. et al. (1991), "Second Structural Motif for Recognition of DNA by Oligonucleotide–Directed Triple–Helix Formation", *Science* 251:1360–1363.

Pilch, D. S. et al. (1991), "Structure, Stability, and Thermodynamics of a Short Intermolecular Purine–Purine–Pyrimidine Triple Helix", *Biochemistry* 30:6081–6087.

Orson, F. H. et al. (1991), "Oligonucleotide inhibition of IL2RαmRNA transcription by promoter region collinear triplex formation in lymphocytes", *Nucleic Acids Res.* 19:3435–3441.

Ferrin, L. J. et al. (1991) "Selective Cleavage of Human DNA: RecA–Assisted Restriction Endonuclease (RARE) Cleavage", *Science* 254:1494–1497.

Pulleyblank, D. E. et al. (1985), "A Structural Basis for S1 Nuclease Sensitivity of Double–Stranded DNA", *Cell* 42:271–280.

Ito, T. et al. (1991), "An Improved Pulsed–Field Polyacrylamide Gel Electrophoresis System for Physical Selection of Linking Clones: Isolation of *SfiI* Linking Clones from a Chromosome 21–Specific Library", *Genomics* 9:707–712.

Feener, C. A. et al. (1991), "Rapid Detection of CA Polymorphisms in Cloned DNA: Application to the 5'Region of the Dystrophin Gene", *Am. J. Hum. Genet.* 48:621–627.

Strobel, S. A. et al. (1990), "Site–Specific Cleavage of a Yeast Chromosome by Oligonucleotide–Directed Triple–Helix Formation", *Science* 249:73–75.

Pei, D. et al. (1991), "A Combinatorial Approach Toward DNA Recognition", *Science* 253:1408–1411.

Tijssen, P., "Non–immunologic molecular recognition systems used in immunoassays", Chapter 3, in Practice and Theory of Enzyme Immunoassays, *Laboratory Techniques in Biochemistry and Molecular Biology,* vol. 15, (R. H. Burdon and P. H. van Knippenberg, eds.), Elsevier: New York, 1988 (cover pages and p. 21).

Roitt, Ivan, et al., *Immunology, C. V. Mosby Company, Gower Medical Publishing: New York (1989) (cover page and pp. 1.6, 5.1 and 7.1).*

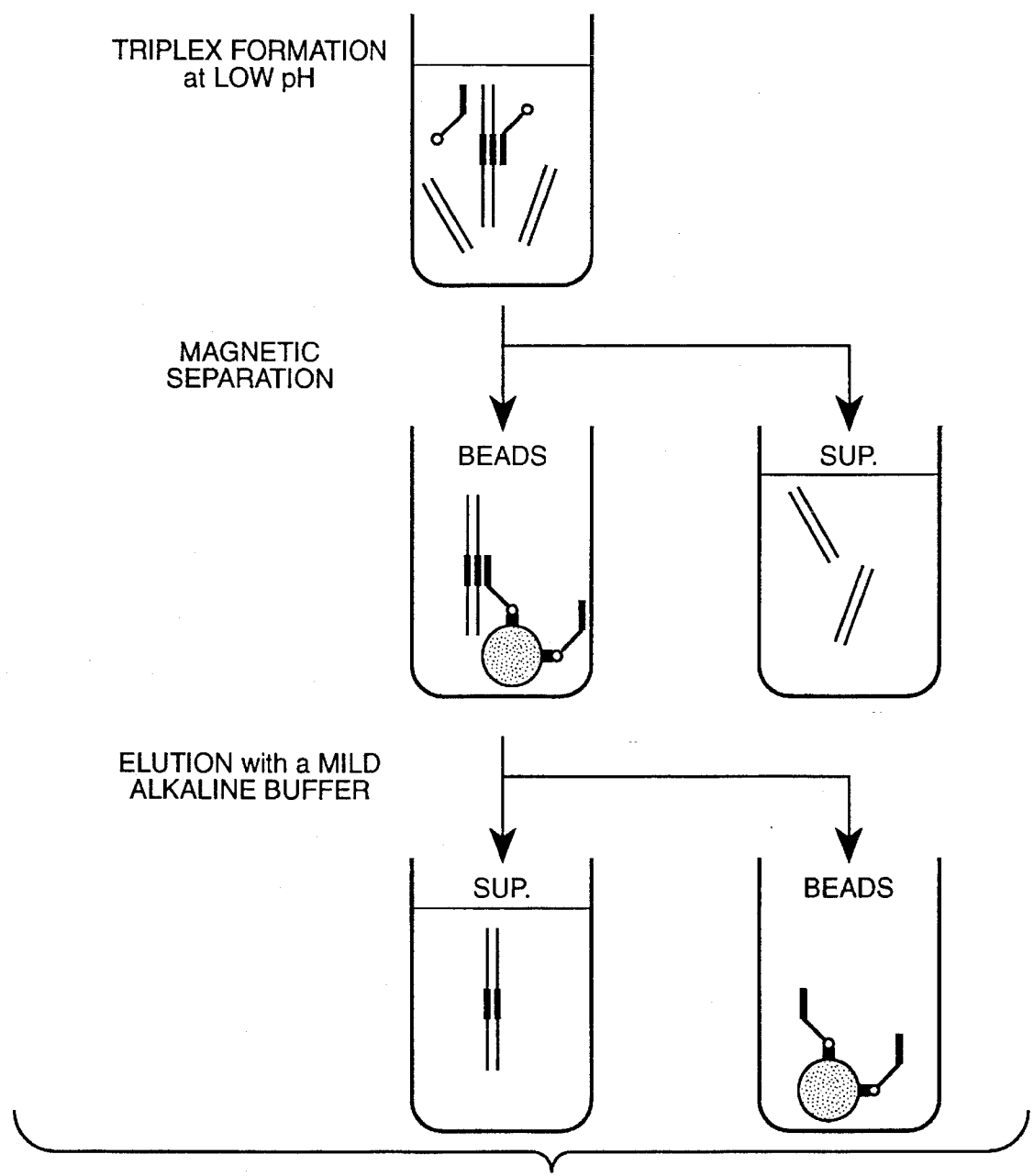
FIG._1

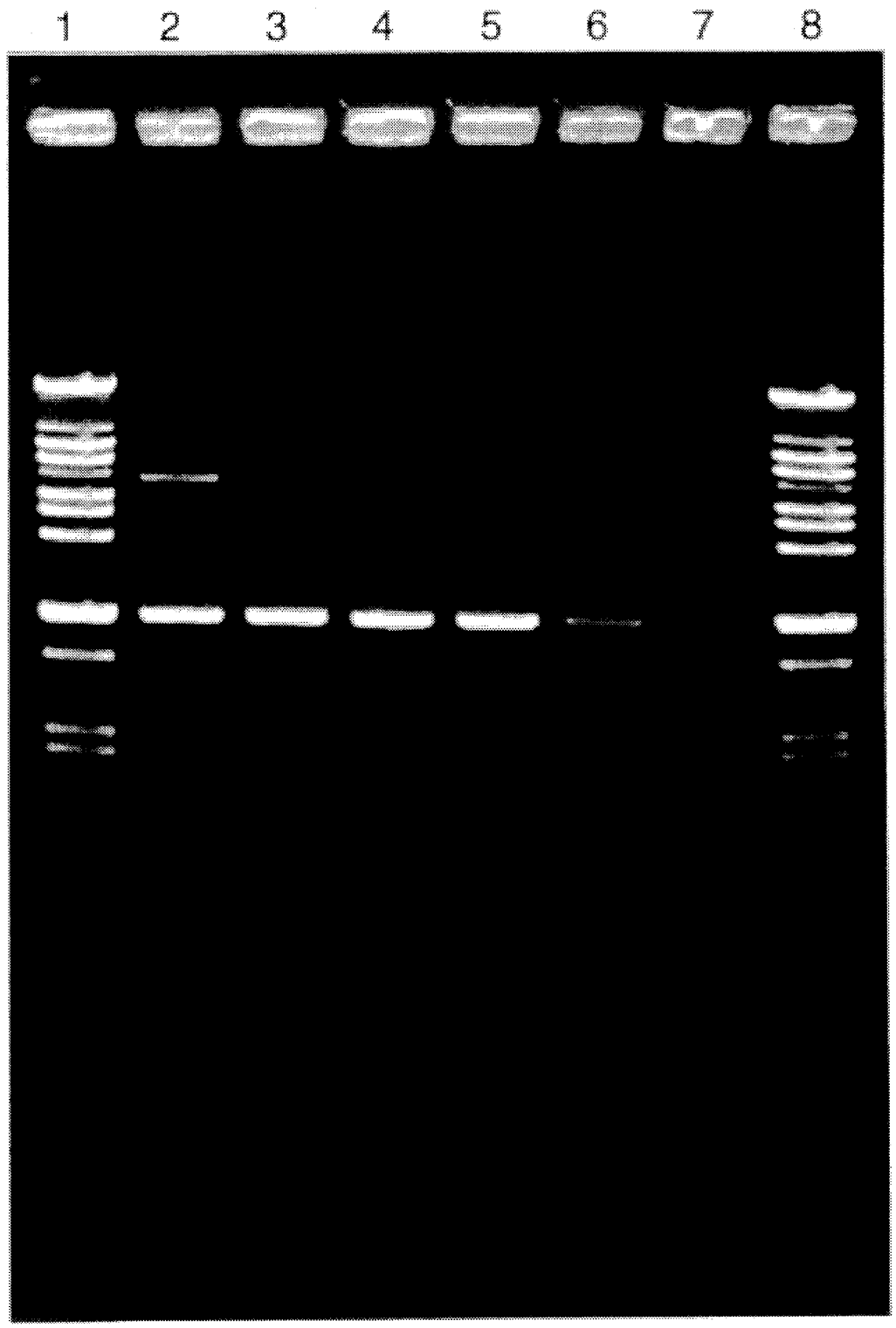
FIG._2

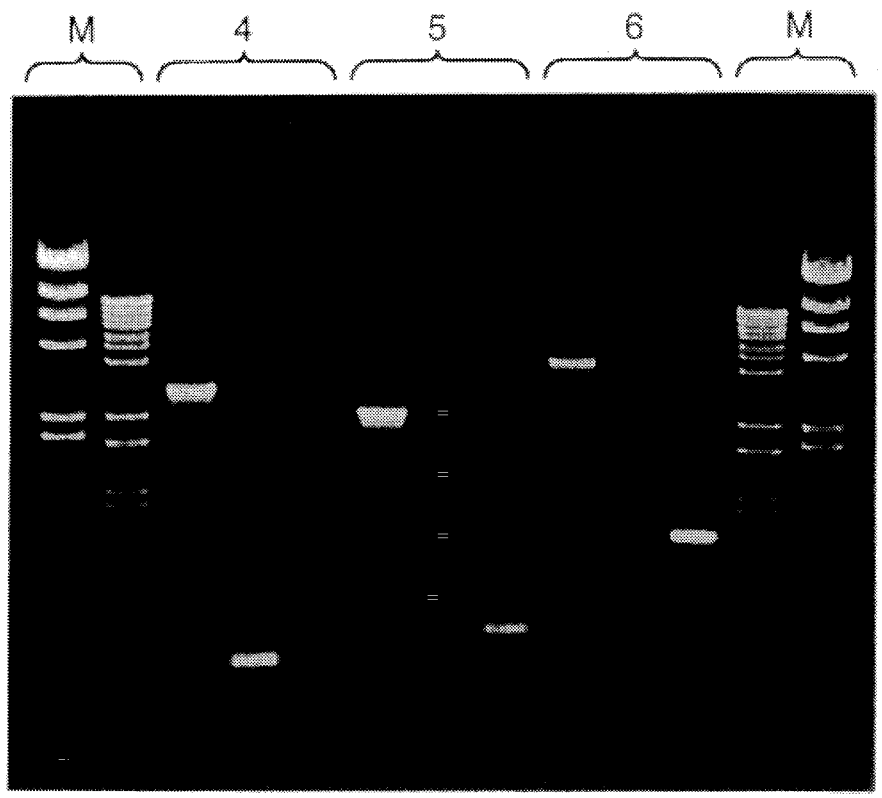
FIG._3A
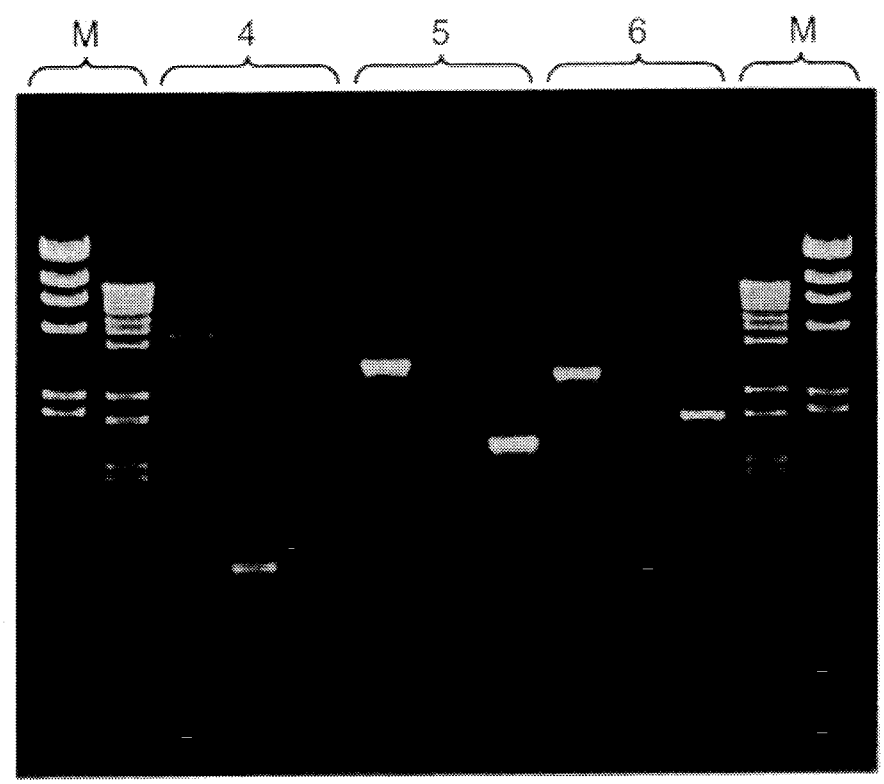
FIG._3B

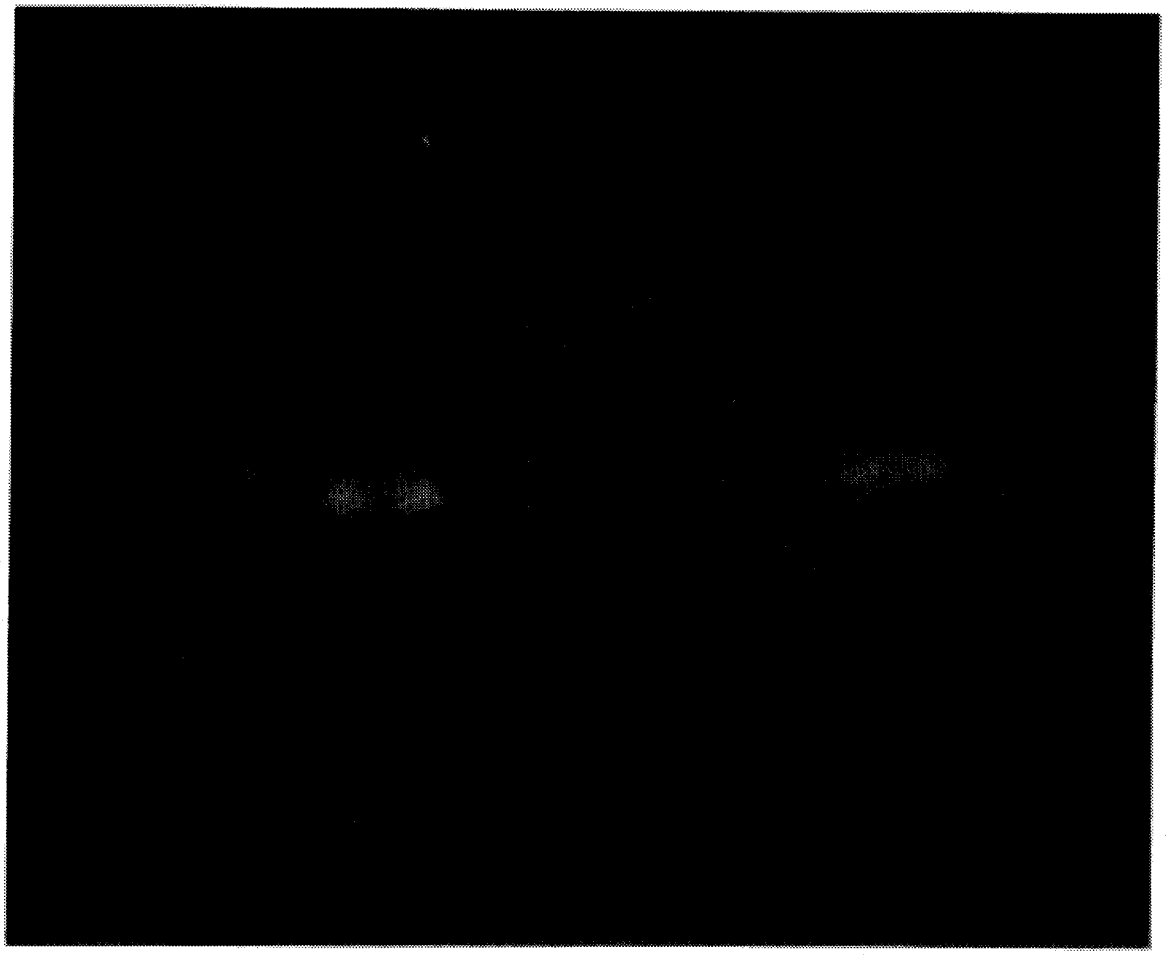
FIG._4

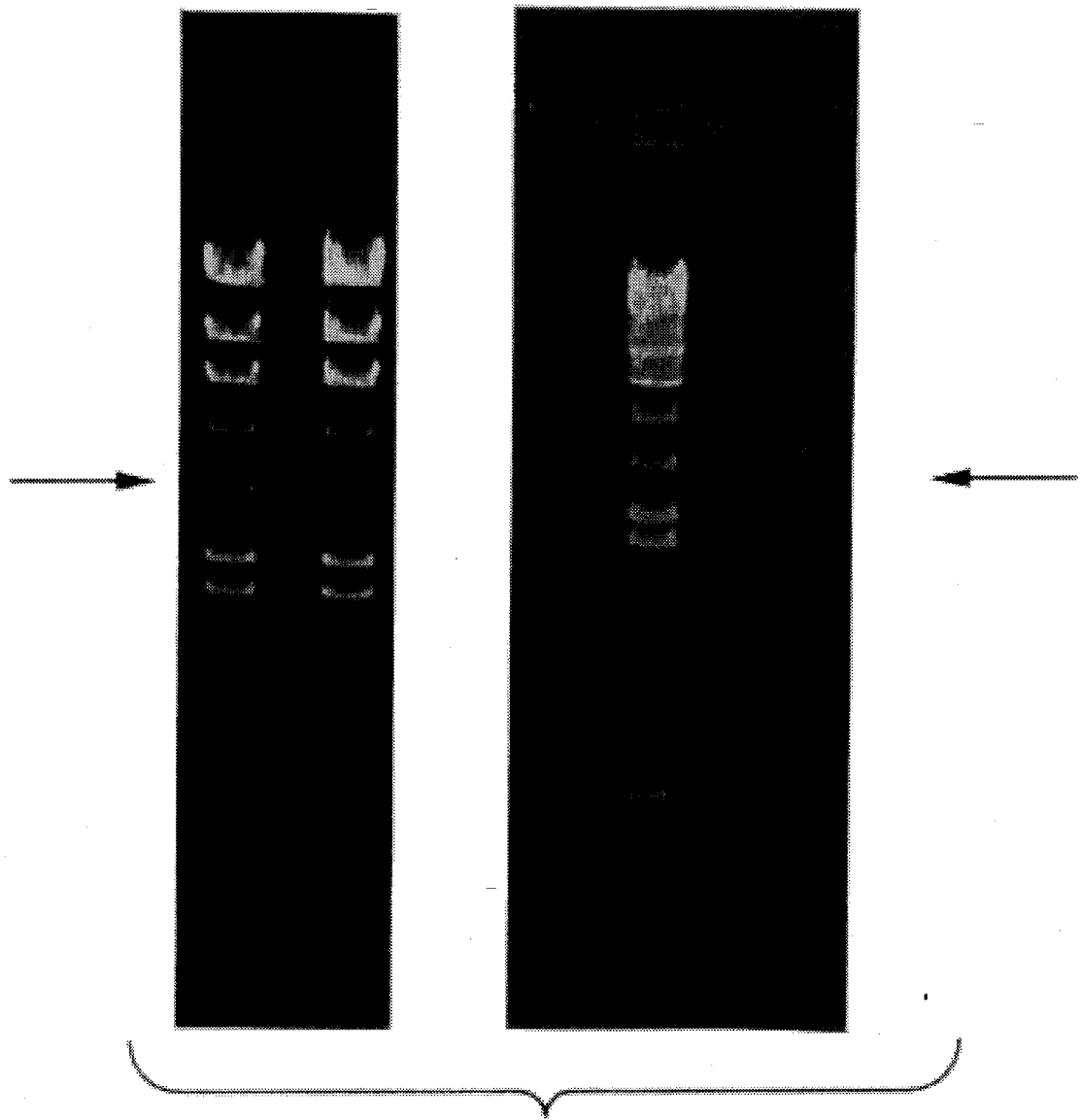
FIG._5

DNA PURIFICATION BY TRIPLEX-AFFINITY CAPTURE AND AFFINITY CAPTURE ELECTROPHORESIS

ACKNOWLEDGEMENTS

This invention was supported in part through grants from the National Cancer Institute, grant number CA39782 and the Department of Energy, contract number DE-AC03-76F00098. The U.S. government has certain rights in this invention.

FIELD OF INVENTION

The present invention relates generally to a method for purifying or isolating double stranded DNA using triple-helix formation and solid phase separation. It also relates to a triple-helix immobilized on a solid phase by means of a molecular recognition system such as avidin/biotin. The present invention further relates to a method for purifying or isolating double stranded DNA by complexing the DNA with a specific binding partner and immobilizing the complex during electrophoresis on a solid phase trap embedded in the electrophoretic gel. The invention still further relates to agarose gels containing a trap comprising a solid phase directly or indirectly fixed with recognition molecules from a molecular recognition system.

BACKGROUND OF THE INVENTION

The first triple-helical structure of nucleic acids was discovered more than 30 years ago (Felsenfeld, G., et al. (1957) *J. Am. Chem. Soc.* 79:2023–2024). While the biological roles of such structures are still open to question, their chemical characteristics have been considerably elucidated in recent works (for review, see Wells, R. D., et al. (1988) *FASEB J.* 2:2939–2949). The most well-characterized triplex is the one formed between a double-stranded homopurine-homopyrimidine helix and a single-stranded homopyrimidine tract. In this type of triple-helix, the third homopyrimidine strand binds to the major groove, parallel to the homopurine strand of Watson-Crick double-helical DNA, via Hoogsteen hydrogen bonding. The third-strand thymine (T) recognizes adenine-thymine (AT) base pairs forming T·A·T triplets, and the third-strand cytosine (C), protonated at its N-3 position, recognizes guanine-cytosine (G·C) base pairs forming $C^+ \cdot G \cdot C$ triplets.

Homopyrimidine oligonucleotides have been shown to form local triplexes with corresponding homopurine sites in larger double-stranded DNAs. Such oligonucleotide-directed triplex formation has been successfully applied in the recent development of sequence-specific artificial rare-cutting endonucleases (Moser, H. E. & Dervan, P. B. (1987) *Science* 238:645–650; Le Doan, T., et al. (1987) *Nucleic Acids Res.* 15:7749–7760), in which oligonucleotides and equipped metal chelates or photoactive groups function as DNA binding and cleaving "domains," respectively. Also, single-site enzymatic cleavage of the yeast genome was achieved by the triplex-mediated "Achilles' heel cleavage" procedure (Strobel, S. A. & Dervan, P. B. (1991) *Nature* (London) 350:172–174), in which a triplex-forming oligonucleotide, instead of a DNA binding protein (Koob, M. and Szybalski, W. (1990) *Science* 250:271–273), was used to protect the targeted single-site from DNA methyltransferase. Such triplex-mediated DNA cleavage techniques provide valuable tools for genome analysis. Specific inhibition of DNA-binding proteins (e.g., transcription factors or replication factors) by triplex formation (Maher, L. J., III, et al. (1989) *Science* 245:725–730; Francois, J.-C., et al. (1989) *Biochemistry* 28:9617–9619; Hanvey, J. C., et al. (1990) *Nucleic Acids Res.* 18:157–161) may provide a principle for the development of antiviral or anticancer drugs. Based on the stability of such triplexes during gel electrophoresis (Lyamichev, V. I. et al. (1988) *Nucleic Acids Res.* 16:2165–2178), a unique procedure for labeling specific DNA fragments was also devised to facilitate restriction mapping of cosmid inserts (Moores, J. C. (1990) *Strategies* 3:23–24, 29).

Typically, specific DNA is isolated from heterogeneous DNA mixtures using conventional hybridization based methods (e.g., colony or plaque hybridization (Sambrook, J., et al. (1989) *Molecular Cloning, A Laboratory Manual*, 2d Ed., Cold Spring Harbor, Cold Spring Harbor Press)). These well-established methods while quite reliable have some practical drawbacks. First, they require time-consuming and labor-intensive steps of filter preparation that often limit the number of clones that can be screened. Furthermore, since these procedures include prior denaturation steps and other treatments that destroy the integrity of the target DNA molecules, one has to reisolate the corresponding clones from the original plates to obtain intact DNA molecules for further biological biochemical manipulations. Third, sequences toxic to the host sometimes hamper successful cloning. Fourth, the natural modifications of the target DNA are not maintained during cloning. Finally, despite recent development of Yeast Artificial Chromosome (YAC) vectors, it is still difficult to clone very large DNAs. Obviously, non-cloning-based biochemical methods to isolate specific DNA from a complex mixture would be of some help with these problems. However, such methods are still not satisfactory. Biochemical purification by density and size fractionation after cleavage with restriction enzymes can be applied only in limited instances (Tsujimoto, Y. and Suzuki, Y. (1984) *Proc. Natl. Acad. Sci. USA* 81:1644–1648). The polymerase chain reaction (PCR) fulfills some of these needs and provides large amounts of DNAs (Mullis, K. B. and Falocna, F. A. (1987) *Methods Enzymol* 155:335–350), but it is currently limited to relatively short (<10 kb) DNA fragments. Furthermore, natural modifications of the original DNA cannot be maintained. Although an effective method of affinity chromatography for DNAs was reported (Tsurui, H. et al. (1990) *Gene* 88:233–239), it requires the prior denaturation of target DNA molecules and elution by denaturation.

Several screening procedures, potentially applicable to large DNAs, that keep the target DNA in its native double stranded form have been developed using RecA protein (Honigberg, S. M., et al. (1986) *Proc. Natl. Acad. Sci. USA* 83:9586–9590; Rigas, B., et al. (1986) *Proc. Natl. Acad. Sci. USA* 83:9591–9595). An affinity capture procedure using hybridization at the end of a large DNA fragment was also reported (Kandpal, R., et al. (1990) *Nucleic Acids Res.* 18:1789–1795). However, these procedures include the handling of DNAs in solution, in at least several steps, which inevitably breaks large DNAs into smaller pieces.

The present invention provides a new rapid method for isolating sequence specific intact double stranded DNA from a heterogeneous mix in a sample by forming an intermolecular triplex with the target DNA and separating the triplex from the mix by means of a solid phase. It also provides a new method for isolating very large sequence specific intact double stranded DNAs by capturing them during electrophoresis on a solid phase embedded in the electrophoretic gel.

SUMMARY OF THE INVENTION

The present invention is a method for isolating double stranded DNA in a sample using triple-helix formation and solid phase separation. The sample is contacted with an oligonucleotide coupled either directly or indirectly to a first recognition molecule of a specific molecular recognition system. A molecular recognition system is a system of at least two molecules which have a high capacity of molecular recognition for each other and a high capacity to specifically bind to each other. The coupled oligonucleotide forms a triple-helix with the particular target DNA by means of Hoogsteen hydrogen bonding. The reaction medium containing the triple-helix is then contacted with a solid carrier to which is either directly or indirectly fixed a second recognition molecule of the molecular recognition system causing the second recognition molecule to specifically bind to the first recognition molecule. The solid phase bearing the triple-helix is then separated from the reaction medium in which the binding between the recognition molecules occurred and the particular target DNA is separated from the oligonucleotide by treating the separated solid phase with a reagent that breaks the bonds between the oligonucleotide and the particular DNA but not between the double helix DNA. The intact particular DNA is then recovered.

In specific embodiments of this triplex-affinity capture method of the invention, the oligonucleotide can be a pyrimidine rich oligonucleotide or a purine rich oligonucleotide. The molecular recognition system can be selected from the group consisting of an antigen/antibody, an avidin/biotin, a streptavidin/biotin, a protein A/Ig (specifically, SpA isolated from *staphylococcus aureus*/immunoglobulin (e.g., IgG)) and a lectin/carbohydrate system. The solid carrier can be selected from a group consisting of numerous materials including plastic, glass, agarose, metal, nitrocellulose, silicon, nylon or silica.

In the preferred embodiment, the molecular recognition system comprises a streptavidin/biotin system. The coupled oligonucleotide comprises a 5'-biotinylated homopyrimidine and the solid carrier to which is fixed the second recognition molecule comprises streptavidin coated magnetic beads. The sample is contacted with the biotinylated homopyrimidine under acid conditions to form a triple-helix between the particular DNA and the oligonucleotide. The reaction medium containing the resulting intermolecular triple-helix is contacted with the streptavidin coated magnetic beads to form a complex comprising the triple-helix and the molecular recognition system attached to the magnetic beads. The magnetic beads bearing the triple-helix are separated from the reaction medium by a magnetic separator and incubated under basic conditions to break the bond between the oligonucleotide and the particular DNA. The particular DNA is then recovered by conventional means.

The present invention further provides a method for isolating a particular intact double stranded DNA in a sample which comprises the steps of incubating a sample containing the particular DNA with a binding partner specific for the DNA for a time sufficient for the binding partner to bind to the particular DNA. The specific binding partner is coupled either directly or indirectly to a first recognition molecule of a specific molecular recognition system. The reaction mixture containing the DNA bound to the coupled binding partner is then electrophoresed in a gel containing a gel-embedded solid phase to which is either directly or indirectly fixed a second recognition molecule of the molecular recognition system. During electrophoresis, the second recognition molecule specifically binds to the first recognition molecule coupled to the specific binding partner bound to the particular DNA. Following electrophoresis, the solid phase is separated from the gel and the particular DNA is separated from the solid phase by treating the solid phase with a reaction medium that breaks the bonds between the DNA and the specific binding partner but not between the double stranded target DNA. The DNA is then recovered.

In specific embodiments, the molecular recognition system can be selected from the group consisting of an antigen/antibody, an avidin/biotin, a streptavidin/biotin, a protein A/Ig and a lectin/carbohydrate system.

In a preferred embodiment, the molecular recognition system is streptavidin/biotin, the DNA specific binding partner coupled to a first recognition molecule comprises a biotinylated uracil containing oligonucleotide, more preferably a biotinylated uracil containing oligodeoxyribonucleotide, which forms complementary base pairs with at least part of the particular target DNA or with an extension of or an attachment to the particular target DNA. Examples of such an oligonucleotide include oligonucleotides with deoxyuracil substituted for thymine or one that has been tailed with poly-dU or poly-dA. The solid carrier to which is fixed a second recognition molecule comprises beads coated with streptavidin and the reagent which breaks the bond between the DNA and the specific binding partner comprises uracil N-glycosylase in a buffer.

In another preferred embodiment, the DNA specific binding partner coupled to a first recognition molecule comprises a 5'-biotinylated homopyrimidine, the solid phase to which is fixed a second recognition molecule comprises streptavidin coated beads and the reaction medium which breaks the bond between the DNA and the biotinylated homopyrimidine is a basic buffer.

Additional embodiments of the invention include a composition comprising triple-helix DNA coupled to biotin bound to a streptavidin or avidin coated solid carrier, an electrophoretic gel wherein within at least one lane of the gel is embedded a particulate, beaded or porous matrix solid phase which is coated with a recognition molecule from a molecular recognition system.

Another embodiment includes an electrophoretic gel having at least one lane with an origin well and a second well in front of the origin well comprising streptavidin or avidin coated plastic, glass or metal beads or particles.

BRIEF DESCRIPTION OF THE DRAWINGS

FIG. 1 shows a schematic representation of the triplex-affinity capture method of the invention.

FIG. 2 is a photograph of an agarose gel following electrophoresis of DNA subjected to the triplex-affinity capture method of the invention.

FIG. 3A represents a photograph of an electrophoretic agarose gel showing the results of a PCR-based assay for $(dT-dC)_n-(dG-dA)_n$ sequences on clones purified by the triplex-affinity capture method of the invention from a chromosome 21 specific library. The gel contains DNA from purified clones 1 and 3 and digested λ DNA following electrophoresis.

FIG. 3B represents a photograph of an electrophoretic agarose gel showing the results of a PCR-based assay for $(dT-dC)_n-(dG-dA)_n$ sequences on clones purified by the triplex-affinity capture method of the invention from a chromosome 21 specific library. The gel contains DNA from purified clones 4–6 and digested λ DNA following electrophoresis.

FIG. 4 represents a photograph of an ethidium bromide stained electrophoretic agarose gel showing the results of electrophoresing biotinylated triple helical DNA in gels equipped with streptavidin traps in lanes 3 and 4.

FIG. 5 represents a photograph of an ethidium bromide stained electrophoretic agarose gel showing the results of end affinity capture electrophoresis using a uracil containing DNA probe.

DETAILED DESCRIPTION OF THE INVENTION

This invention is directed to a method for purifying intact DNA using intermolecular triple-helix formation and solid phase separation. In this triplex-affinity capture (TAC) method, the DNA being detected in the assay is intact double stranded DNA and the method can be used to capture sequence specific plasmid DNAs. Essentially, the target DNA sequence is a double stranded homopurine-homopyrimidine helix. Nevertheless, the method may be extended by the use of some permissiveness mismatches in triple-helix formation (Griffin, L. C., et al. (1989) *Science* 245:967–971 and Belotserkovskii, B. D., et al. (1990) *Nucleic Acids Res.* 18:6621–6624), alternate strand triple-helix formation (Horne, D. A., et al. (1990) *J. M. Chem. Soc.* 112:2435–2438), other types of triple-helices (Cooney, M., et al. (1988) *Science* 241:456–459; Kohwi, Y., et al. (1988) *Proc. Natl. Acad. Sci. USA* 85:3781–3785; Letai, A. G., et al. (1988) *Biochemistry* 27:9108–9112; Bernues, J., et al. (1989) *EMBO J.* 8:2087–2094; Beal, P. A., et al. (1991) *Science* 251:1360–1363; Pilch, D. S., et al. (1991) *Biochemistry* 30:6081–6087; Orson, F. M., et al. (1991) *Nucleic Acids Res.* 19:3435–3441), including ones formed by recombinase proteins (Hsieh, P., et al. (1990) *Genes Dev.* 4:1951–1963; Rao, B. J., et al. (1991) *Proc. Natl. Acad. Sci. USA* 88:2984–2988) and artificial base analogs.

The TAC procedure of the invention is especially appropriate for isolating $(dT-dC)_n \cdot (dG-dA)_n$ dinucleotide repeats from human genome. This sequence is a member of so-called "microsatellite" DNAs distributed throughout mammalian genomes (Manor, H., et al. (1988) *J. Mol. Evol.* 27:96–101; Wong, A. K. C., et al. (1990) *Chromosoma* 99:344–351). It is often hyper-variable in the number of repeat units (n) from individual-to-individual and thus provides highly informative DNA markers for genetic linkage mapping (Tautz, D. (1989) *Nucleic Acids Res.* 17:6463–6471; Love, J. M., et al. (1990) *Nucleic Acids Res.* 18:4123–4130; Moore, S. S., et al. (1991) *Genomics* 10:654–660; Weber, J. L. (1990) in Genome Analysis, eds. Davies, K. E. et al. (Cold Spring Harbor Lab., Cold Spring Harbor, N.Y.). Vol. 1, pp. 159–181). The TAC method may also be used for the effective enrichment of triplex forming single copy sequences from yeast and more complex genomes using the appropriate probes. The use of G and a novel artificial base analog (Kiessling, L. L., et al. (1992) *Biochemistry* 31:2829–2834) in the third strand has broadened the triplex recognition capability to allow one to find a target for TAC in natural non-tagged sequences with much ease.

The TAC method for purifying a particular double strand of DNA comprises contacting the sample with an oligonucleotide coupled either directly or indirectly to a first recognition molecule of a specific molecular recognition system. The oligonucleotide is designed to specifically form a triple helix with the target DNA. Methods for designing such oligonucleotides depend on the target DNA. Acceptable methods are set forth in Kiessling, L. L., et al. (1992) *Biochemistry* 31:2829–2834; Durland, R. H., et al. (1991) *Biochemistry* 30:9246–9255; Beal, P. A., et al. (1992) *Nucleic Acids Res.* 20:2773–2776; Giovannangeli, C., et al. (1992) *PNAS* 89:8631–8635; Beal, P. A., et al., (1992) *J. Am. Chem. Soc.* 114:4976–4982. Oligonucleotides which contain deoxyuracil for thymine at least along part of the chain are acceptable oligonucleotides. Oligonucleotide backbone analogs such as polyamide nucleic acids and phosphotriesters will form a triplex with double stranded DNA and can also be used in the TAC method of the invention.

The triplexes formed between the specific oligonucleotides and the target DNA molecules containing the corresponding homopurine-homopyrimidine sequences are subsequently contacted with a solid carrier to which is either directly or indirectly fixed a second recognition molecule belonging to the same molecular recognition system as the first recognition molecule coupled to the oligonucleotide. The second recognition molecule is a molecule which will specifically bind to the first recognition molecule. The solid phase is subsequently separated from the reaction medium where the binding occurred and therefore is also separated from any remaining non-triplexed nucleic acids. Finally, the target DNAs are recovered in intact double stranded form by treating the separated solid phase bearing the triple-helix with a reagent that breaks the bonds between the oligonucleotide and the particular DNA but not between the double helix DNA. The particular DNA is then recovered.

Using several methods well-known in the art including electrophoresis and fluorometry, the TAC method can also be used to determine the presence or absence of a particular double stranded DNA in a sample by testing for the presence of the particular DNA in the eluate after the triple helix separation step.

Although words used herein have their normal meanings when applied generally to the invention, the following definitions apply to preferred embodiments of the invention.

A "oligonucleotide" as used herein is defined as a molecule comprised of about eight or more deoxyribonucleotides or ribonucleotides. Several factors will determine the exact size of the oligonucleotide including binding affinity and specificity (see, Strobel, S. A., et al (1990) *Science* 249:73–75, for a discussion of probe length).

A "polynucleotide" as used herein is defined as a molecule comprised of deoxyribonucleotides or ribonucleotides greater than 100-mer.

A "molecular recognition system" is a system of at least two molecules which have a high capacity of molecular recognition for each other and a high capacity to specifically bind to each other. Molecular recognition systems for use in the invention are conventional and are not described here in detail. Techniques for preparing and utilizing such systems are well-known in the literature and are exemplified in the publication Tijssen, P., *Laboratory Techniques in Biochemistry and Molecular Biology Practice and Theories of Enzyme Immunoassays*, (1988), eds. Burdon and Knippenberg, New York:Elsevier.

The terms "bind" or "bound", etc. include both covalent and non-covalent associations, but can also include other molecular associations where appropriate such as Hoogsteen hydrogen bonding and Watson-Crick hydrogen bonding.

For use in the present invention, the oligonucleotide is preferably a homopyrimidine oligonucleotide $(T-C)_n$. But a purine-rich oligonucleotide which binds to double stranded DNA at neutral pH in the presence of multivalent cations (e.g., spermine or $Mg^{2+}$) to form a second type of triplex (Cooney, M., et al. (1988) *Science* 241:456–459; Beal, P. A., et al. (1991) *Science* 251:1360–1363) may also be used. After solid phase separation of this type of triplex by using a specific molecular recognition system, the triplex bond can be broken by incubating the solid phase containing the triplex in a buffer containing EDTA or any other magnesium chelate to chelate divalent cations and release the target DNA. This type of triplex is not affected by the non-specific interaction between DNA and streptavidin and therefore enables the use of fairly non problematic electrophoretic buffers in the electrophoretic capture aspects of the invention.

Acceptable molecular recognition systems for use in the present invention include but are not limited to an antigen/antibody, an avidin/biotin, a streptavidin/biotin, a protein A/Ig and a lectin/carbohydrate system. The preferred embodiment of the invention uses the streptavidin/biotin molecular recognition system and the preferred oligonucleotide is a 5'-biotinylated homopyrimidine oligonucleotide. To form the intermolecular triple-helices, the sample containing the DNA is incubated in an acidic buffer with the biotinylated nucleotide. A mildly acidic buffer of pH 4.5–5.5 is preferred but acidic buffers ranging from a pH of about 3.5 to about 6.5 are acceptable. The preferred buffer is a sodium acetate/acetic acid buffer but other buffers such as sodium/citrate/citric acid, PIPES and sodium phosphate may also be used. With reactions at high pHs (6.0 or above), sodium phosphate buffer is used instead of sodium acetate/acetic acid buffer. The reaction medium containing the triple-helices is then incubated with the solid carrier fixed with the second recognition molecule of the molecular recognition system. The solid phase is preferably suspended in the same buffer as the buffer used to induce triple-helix formation. Again, the second recognition molecule must be a recognition molecule with high a affinity for the recognition molecule coupled to the oligonucleotide. When the recognition molecule coupled to the oligonucleotide is biotin, a preferred solid phase is a streptavidin coated solid phase. If the first recognition molecule coupled to the oligonucleotide is streptavidin, then the preferred second recognition molecule attached to the solid phase would be a biotin. When appropriate, the recognition molecules may be directly or indirectly coupled to the oligonucleotide or solid phase. However, if the recognition molecules are indirectly attached to the oligonucleotide, the problems of steric hindrance should be considered. For example, if streptavidin or avidin are chemically attached to oligonucleotides via linkers, care must be taken with respect to the length of the linker. Too short linkers may cause steric hindrance and result in low recovery. An example of an acceptable molecular recognition systems other than streptavidin/biotin system that may be used with the TAC method of the invention is the antigen/antibody system. An appropriate example of this system is the digoxigenin antigen and an anti-digoxigenin antibody system. (See, Current Protocol in Molecular Biology, (Eds. Ausbel, F. M., et al.), Supl. 12, Greene Publishing Associates and Wiley-Interscience, 1990.)

Numerous materials and structures may be employed for the actual solid carrier portion of the solid phase. As defined herein, a solid phase includes the solid carrier and any substance directly or indirectly fixed to the carrier. Suitable solid carrier materials include agarose, cellulose, nitrocellulose, cross-linked dextrose, silicon, silica, nylon, glass, metallic and magnetic compositions and numerous plastics. Preferred structures are particles or beads but tubes, disks and microplates are also acceptable. The second recognition molecule may be coated on the solid carrier or they may be covalently bonded or non-covalently bonded or cross-linked to the support. Preferably, the solid carrier comprises magnetic beads. However, for example, agarose beads have also been used successfully with the TAC method of this invention. The time period for incubating the solid phase with the triplex coupled to the first recognition molecule will depend upon the particular molecular recognition system. When the molecular recognition system is streptavidin/biotin, a period of about one hour is preferred, but periods from about 5 minutes to about 48 hours are also acceptable. When the recognition molecule on the carrier is streptavidin the ionic strength of the reaction buffer should be high (e.g., from about 1.5 to about 2.5) so as to reduce any non-specific interaction between the DNA and the streptavidin. Addition of appropriate detergents (e.g., 0.02% SDS) can also be used for the elimination of non-specific interaction between DNA and the streptavidin.

In an alternative procedure, the probe (e.g., oligonucleotide) coupled to the first recognition molecule and the solid phase bearing the second recognition molecule may be simultaneously added to the sample containing the DNA, for purposes of acquiring a triple helix immobilized to a solid phase. In another alternative procedure, prior to triplex formation, the first recognition molecule coupled to the oligonucleotide may first be bound to the solid phase by being first incubated with the solid carrier bearing the second recognition molecule. The resulting solid phase bearing the immobilized oligonucleotide can then be introduced into a sample for purposes of forming a triple helix with the particular targeted DNA.

Following incubation and the immobilization of the triplex on the solid phase following either binding of the first recognition molecule to the second recognition molecule or following triplex formation, the solid phase bearing the triplex is separated from the reaction medium. The method of separation will depend upon the type of solid carrier used. Separation can occur by draining the reaction medium off of and away from the solid phase and or washing the solid phase. When the solid carrier is the preferred magnetic beads, the beads can be separated by a magnetic particle concentrator and washed with buffer (see, Uhlen, M. (1989) *Nature* (London) 340:733–734). Finally, the solid phase is incubated with a reagent which will break the Hoogsteen hydrogen bonds between the DNA and the oligonucleotide. Preferably, the reagent is a basic buffer with a pH ranging from about 8.0 to about 13.0. More preferably, from about 8.0 to about 10.0. Most preferably, 1.0M Tris·HCl, in 0.5 MEDTA at a pH of about 9. However, other buffers such as TE (10 mM Tris-HCl (pH 8), 1 mM EDTA are also acceptable. Again, incubation time will depend upon the choice of the reagent. Care should be taken that the reagent used to break the bonds between the DNA and the oligonucleotide breaks only the Hoogsteen hydrogen bonds and not the Watson and Crick double helical DNA bonds. Triplexes using oligonucleotide backbone analogs can be formed and broken under conditions or reagents similar to those used for regular oligonucleotides. Following separation of the target DNA from the oligonucleotide, the intact target double stranded DNA is recovered from the eluate by conventional means such as phenyl/chloroform extraction (1:1 (vol/vol) and ethanol precipitation or electrophoresis.

This method can also be used to determine the presence or absence of the particular target DNA by electrophoresis of the eluate or by conducting a fluorometric assay of the eluate.

This invention is further directed to a method for purifying sequence specific DNA and large intact DNA (i.e., greater than 100,000 base pairs) by binding the particular DNA to a specific binding partner coupled to a molecular recognition molecule and immobilizing the bound DNA during electrophoresis on a solid phase trap bearing a second recognition molecule wherein the trap is embedded in the electrophoretic gel. This affinity capture electrophoresis (ACE) method selectively captures the large target DNA molecule bound to its specific binding partner while the other non-target molecules pass through the trap.

In one preferred ACE embodiment using the TAC method of the invention discussed above, the target DNA is a homopurine-homopyrimidine block or a DNA that contains a homopurine-homopyrimidine block or homopurine-homopyrimidine blocks. The target DNA may also comprise other DNAs which can form triple-helices with the specific binding partner. Examples of such DNAs were previously discussed in conjunction with the TAC method.

In another of the preferred embodiments, the target DNA comprises DNA fragments the ends of which have been converted to single stranded DNA. However, this method can also isolate any DNAs if RecA or similar recombinase proteins are used to assist triple helix formation between the probe and the target DNA sequence. (Ferrin, L. J., et al., (1991) *Science* 254:1494–1497. In the ACE method of the invention, the bound target DNA is attached to a solid phase which is too large to migrate through the gel pores during electrophoresis. The preferred gel material is agarose but polyacrylamide, other synthetic polymer gels or any convective but hydrophilic medium can also be used. The targeted DNA is selectively trapped while the other non-target molecules pass through the trap. The trap is then separated from the gel. After separation, the trap is treated with appropriate reagents which destroy the bonds between the coupled specific binding partner probe and the desired DNA. This treatment releases the target DNA and allows purification of the intact DNA.

As previously stated, one of the preferred embodiments of the affinity capture electrophoresis method of the invention uses a procedure very similar to the triplex-affinity capture method described above. In the TAC electrophoresis method, the target DNAs, the coupled oligonucleotide probes, oligonucleotide backbone analogs such as polyamide nucleic acids and phosphotriesters, the molecular recognition systems and the solid carriers are the ones used and discussed above for the TAC method. However, coupled ribonucleotides or coupled polynucleotides can also be used to form a triplex or a triplex equivalent and capture intact DNA. Except for reasons which are obvious, solid carriers such as discs, tubes, microplates, etc., are not acceptable. Again, preferably the target DNA contains a double stranded homopurine-homopyrimidine helix. But, again, as discussed above, other types of DNA may also be used. The preferred specific binding partner is a pyrimidine-rich oligonucleotide probe, preferably $(T-C)_n$ but other probes including a purine rich oligonucleotide can also be used. The oligonucleotide or other specific binding partner is coupled to a first recognition molecule, preferably biotin or streptavidin. Again, however, the specific binding partner may also be coupled to molecular recognition molecules belonging to other systems including an antigen/antibody, a protein A/Ig, or a lectin/carbohydrate system. The specific binding partner may be coupled either directly or indirectly to the recognition molecule but, again, care must be taken with indirect coupling to avoid steric hindrance. A preferred specific binding partner is a 5'-biotinylated homopyrimidine oligonucleotide. The sample and the biotinylated oligonucleotide are incubated in a mildly acidic buffer such as sodium acetate buffer (preferably pH approximately 4.5–5.0) but other buffers such as sodium citrate or sodium phosphate having pHs ranging from about 3.5 to about 6.5 as described above may also be used to form the intermolecular triple-helices. Following triplex formation, the mixture is electrophoresed in the gel containing the trap. The trap is a solid carrier preferably uniform glass, plastic or metal beads or particles but other solid phases may also be used providing they are large enough to stay embedded in the gel, will not migrate through the pores of the gel and can be separated from the gel following electrophoresis. A second recognition molecule which corresponds to the first recognition molecule coupled to the probe is attached to the solid carrier to form the solid phase trap. Again, the recognition molecule may be directly or indirectly attached to the solid carrier but care must be taken to prevent interference with the migration of the undesired molecules as well as to prevent steric hindrance. Preferably, the trap is streptavidin uniform coated beads. This trap is preferably prepared by allowing a suspension of beads fixed to the appropriate recognition molecules to solidify in a second well which is placed in front of the origin well of the same lane. In general, the exact amount of the solid phase and the percentage of gel material in the suspension used to prepare the trap will depend upon the amount of material being electrophoresed as well as the percentage of actual gel material (i.e., agarose) in the entire gel. However, in general the percentage of the gel material in the trap will be slightly higher than the percentage of gel material in the entire gel. For example, in an 0.8% agarose gel (0.8%, LE agarose, FMC), an appropriate trap, approximately 1 millimeter thick, is made by allowing a suspension (approximately 5 mgs/ml final concentration) of streptavidin-coated magnetic beads (Dynabeads, streptavidin M-280, Dynal) in 1% molten Inert Agarose (FMC) to solidify. Care must also be taken to maintain the pH of the gel during electrophoresis at a pH which is stable for triplex maintenance. When the TAC method is used in conjunction with affinity capture electrophoresis and the molecular recognition system is a streptavidin, avidin/biotin system, the mixture containing the triple-helices should be electrophoresed in a high ionic strength buffer to minimize non-specific interaction between DNA and streptavidin at acid pH. An alternative solution to the non-specific interaction problem is the use of modified streptavidin. For example, succinylation of the streptavidin-beads reduced the non-specific interaction with DNA at acidic pH, although not completely (data not shown). It would be possible to prepare streptavidin with an even more acidic isoelectric point by site-directed mutagenesis using a recently-developed expression system for this protein (Sano, T. and Cantor, C. R. (1990) *Proc. Natl. Acad. Sci. USA* 87:142–146). Preferably, electrophoresis is done under cold conditions (about 4° C.) but the temperature may range from about 4° C. to about 40° C. Following electrophoresis, the trap can be removed and treated with alkaline buffer such as 1.0 molar Tris·HCl, pH 9/0.5 mM EDTA for a time sufficient to break the Hoogsteen hydrogen bonds between the double-helix DNA and the homopyrimidine probe but not the Watson-Crick bonds between the double-helical DNA. Other buffers which can be used to separate the DNA from the solid phase are TE (10 mM Tris-HCl(pH8), 10 mM EDTA or other similar buffers with pHs ranging from about 8.0 to about 13.0, preferably 8.0 to 10.0. If the probe (i.e., specific binding partner) is a ribooligonucleotide, the pH of the buffer should be no higher than about 8.5. The incubation period used for separating the DNA will depend on the reagent used. When Tris·HCl is used, the time for incubation can vary from about 5 minutes to 2 hours but 20 minutes is usually sufficient. The separated target DNA can then be recovered from the eluate by standard means such as 1:1 (vol/vol) phenol/chloroform extraction and ethanol precipitation.

In another preferred embodiment of the affinity capture electrophoresis method of this invention, DNAs which do not contain homopurine/homopyrimidine tracts can be isolated by using their ends as targets. Oligonucleotides using deoxyuracil for thymine and ribooligonucleotides are especially suited for "end capture" ACE.

In one procedure where the end sequence of the particular DNA is known a sample containing the particular DNA can be treated with an exonuclease (such as T7 gene 6 exonuclease, λ exonuclease and exonuclease III) to convert each DNA end into a single stranded form, and then incubated with a biotinylated uracil-containing oligodeoxyribonucleotide or RNA probe including oligoribonucleotide corresponding to the particular end of the DNA under the appropriate conditions for a time sufficient for hybridization between the end and the probe to occur. The reaction mixture containing the hybridized ends can then be electrophoresed in a gel containing immobilized streptavidin coated beads trapping the end hybridized DNA by binding the biotin to the streptavidin coated beads. The solid phase bearing the particular DNA is then separated from the gel following electrophoresis and the particular DNA is separated from the solid phase with a buffer containing uracil N-glycosylase (UNG) or RNaseH, depending on the probe, to break the bonds between the DNA and the specific binding partner probe. The DNA can then be recovered by conventional means.

In another procedure, a sample containing the particular DNA, the end of which can serve as a selective substrate for terminal deoxyribonucleotidyl transferase (TdT), can be treated with TdT and dUTP or dATP, followed by incubation with a biotinylated oligonucleotide tailed with dUTP or dATP, respectively, for a time sufficient for hybridization between the both tails to occur.

For example, the target DNA is tailed with dA, whereas the corresponding binding partner is tailed with dU, so that both are complementary to form a duplex. Alternatively, as discussed above, the ends of the target DNA are converted to single-strands by the use of various exonucleases, while the corresponding dU-containing probe can be prepared by PCR or chemical synthesis if the nucleotide sequences of the ends are known. Following entrapment, the trap can be removed from the gel and treated in situ with an enzyme or reagent that breaks or destabilizes the duplex between the specific probe and target portion but not other double stranded portion. The DNA can then be recovered using standard procedures such as those described above. In a particular embodiment, the specific binding partner is a poly-dU-tailed oligonucleotide prepared to correspond to a poly-dA-tailed target DNA fragment. Usually, the particular DNA is obtained from a plasmid which has been linearized by digestion with a restriction enzyme and tailed with dATP using terminal deoxynucleotidyl transferase. Separately, a biotinylated oligonucleotide is tailed with dUTP for use as a probe. Again, the recognition molecule may belong to groups other than biotin/streptavidin or avidin/biotin but in choosing a particular molecular recognition system, the conditions required to maintain the desired coupling of the recognition molecule on the probe and also the desired bonding during electrophoresis should be carefully considered. In this embodiment of the method the sample and probe are mixed in an appropriate medium that permits complementary base pairing between the tails of the target DNA and the probe. A preferred medium is TE buffer (Sambrook, J., et al.: Molecular Cloning, A Laboratory Manual, 2nd Ed., Cold Spring Harbor, Cold Spring Harbor Press, 1989) containing NaCl and loaded onto an electrophoretic gel equipped with the appropriate trap. In the instance where the specific binding partner is a biotinylated poly-dU tailed oligonucleotide, TBE buffer (Sambrook, J., et al. ibid) is preferred. After the run, the trap is removed from the gel and incubated in TBE buffer containing an appropriate amount of a reagent which breaks the hydrogen bonds resulting from the complementary-based pairing between the poly-A and poly-U. A preferred reagent for breaking these bonds is uracil N-glycosylase (UNG; Perkin Elmer, Cetus). The amount of UNG will depend on the amount of target DNA and the size of the trap. Appropriate buffers other than TBE that can be used are TAE or other buffers recommended by suppliers. Incubation with TBE should occur around 37° C. but can be done from about 25° C. to about 42° C. A preferred time is one hour. However, the incubation period again will depend upon the reagent used and can vary from about 30 mins. to about 2 hours for purposes of bond separation depending on the amount of DNA trapped. Following separation of the target DNA from the specific binding partner, the intact large target DNA may be recovered by standard procedures and can be used for bacterial transformation or gel electrophoresis. The presence or absence of a particular target DNA can also be determined with the ACE method by subjecting the eluate to various treatments, such as a second electrophoresis, following DNA and probe separation.

In addition to the ACE capturing strategies described above, the use of recombinase proteins such as RecA protein is a promising approach to broaden the applicability of ACE. Such proteins have been shown to make recombination intermediates that are stable during electrophoresis (Hsieh, P. et al. (1990) *Genes Dev.* 4:1951–1963; Rao, B. J. et al. (1991) *Proc. Natl. Acad. Sci USA* 88:2984–2988) and would allow any sequence to serve as the target of a capturing probe. The recent finding that the complex formed between RecA protein and an oligonucleotide probe can find a homologous sequence in genomic DNA embedded in agarose beads (Ferrin, L. J., et al. (1991) *Science* 254:1494–1497) encourages the application of this approach to very large DNAs.

Another interesting variation of this invention would be multiplexing or using two or more different traps so as to isolate two or more different targets from a single mixture. Combined use of other efficient labeling and molecular recognition capturing systems (e.g., digoxigenin and anti-digoxigenin antibody) with the biotin-streptavidin system would enable one to recover multiple target DNAs from a single electrophoretic lane containing multiple traps for individual labeling-capturing systems.

The invention having been generally described is better understood by reference to the following detailed examples. These examples are provided for illustration only and are not intended to be limiting of the invention unless so stated.

EXAMPLES

Example 1

The invention was demonstrated using a plasmid containing a known T–C repeat and plasmids prepared from a human genome library.

Materials

Plasmid pTC45 (Pulleyblank, D. E., Haniford, D. B. & Morgan, A. R. (1982) *Cell* 42:271–280) was a generous gift from J. S. Lee (University of Saskatchewan). An oligonucleotide BTC-20 [5'-biotinylated (T–C)$_{10}$] (SEQ ID NO:1) was synthesized by Operon Technologies (Alameda, Calif.). A human chromosome 21-specific plasmid library was/prepared as described (Ito, T., et al. (1991) *Genomics* 9:707–712). Streptavidin-coated magnetic beads (Dynabeads Streptavidin M-280) and a magnetic particle concentrator (Dynal MPC-6) were obtained from Dynal (Great Neck, N.Y.). Forward (24-mer) and reverse (22-mer) pUC/M13 sequencing primers were obtained from Promega. Restriction endonucleases and Taq DNA polymerases were purchased from New England Biolabs and Perkin Elmer/Cetus, respectively. DNA ligation kit was obtained from Takara Biochemical (Berkeley, Calif.).

Triplex Affinity Capture Procedure

Plasmid DNA (~2 μg) was incubated with 20 pmol of biotinylated oligonucleotides in 50 μl of buffer B (2.0M NaCl/0.2M sodium acetate/acetic acetic acid, pH 4.5–5.5) at 50° C. for 2 hr. (Note that the pH values were measured at room temperature after addition of NaCl.) For reactions at higher pH (6.0 or above), sodium phosphate buffer was used instead of sodium acetate/acetic acid buffer. Streptavidin-coated magnetic beads (50 μl), washed with and resuspended in buffer B (50 μl) were added to the mixture. After further incubation for 1 hr, the beads were separated by a magnetic particle concentrator and washed eight times with 0.5 ml of the same buffer. Finally, the beads were incubated with buffer E (1.0M Tris·HCl, pH 9/0.5 mM EDTA) for 20 min. DNA was recovered from the eluate by 1:1 (vol/vol) phenol/chloroform extraction and ethanol precipitation and was used for bacterial transformation or gel electrophoresis.

Isolation and Analysis of Dinucleotide Repeat Clones

Plasmids prepared from a chromosome 21-specific library were linearized by digestion at a unique HindIII site on each clone and subjected to the procedure described above at pH 5.5. Recovered DNAs recirculized by self-ligation using DNA concentrations of ~0.1 μg/ml were used for transformation of competent *Escherichia coli* DH5α cells. Transformant plasmids were assayed for the presence of the repeat by a polymerase chain reaction (PCR)-based method as described (Feener, C. A., Boyce, F. M. & Kunkel, L. M. (1991) *Am. J. Hum. Genet.* 48:621–627). Thermal cycling parameters were as follows: initial denaturation at 95° C. for 4 min; 24 cycles of denaturation at 94° C. at 1 min, annealing at 55° C. or 58° C. for 1 min, and extension at 72° C. for 3 min; and a final cycle with an extension time of 10 min. Primers used were forward or reverse sequencing primers and a 27-mer oligonucleotide BamTC [CCCGGATCC(TC)$_9$] (SEQ ID NO:2). PCR products were electrophoresed on agarose gels and detected by staining with ethidium bromide.

Principle of Triplex Affinity Capture

The procedure is schematically illustrated in FIG. 1. First, biotinylated homopyrimidine oligonucleotides are incubated with a DNA mixture under a mild acidic condition, which promotes protonation of cytosine and, thus, triplex formation. The triplexes formed between the oligonucleotides and target DNA molecules, containing the corresponding homopurine-homopyrimidine sequences, are subsequently bound to streptavidin-coated magnetic beads and magnetically separated from other non-triplex-DNAs. Finally, the target DNAs are recovered in double-stranded form by incubating the beads under a mild alkaline condition which destabilizes Hoogsteen hydrogen bonding (triple helix) but not Watson-Crick base pairs (double helix).

Evaluation of Basic Conditions by Using a Model System

For the evaluation of basic conditions, an artificially reconstituted plasmid library was prepared by mixing pUC19 and pTC45 (Pulleyblank, D. E., Haniford, D. B. & Morgan, A. R. (1982) *Cell* 42:271–280). The latter plasmid contains a 45-base-pair (bp) run of a simple T–C repeat and forms an intermolecular triplex with exogenously added (T–C)$_n$ oligonucleotide as described (Lyamichev, V. I., Mirkin, S. M., Frank-Kamenetskii, M. D. & Cantor, C. R. (1988) *Nucleic Acids Res.* 16:2165–2178), whereas the former does not (data not shown). A 5'-biotinylated oligonucleotide (BTC-20) (SEQ ID NO:1) was used to capture pTC45 according to the basic scheme described above. Plasmids eluted from the beads were used to transform competent *E. coli* DH5α cells. Since transformants bearing pUC19 and pTC45 form blue and white colonies, respectively, on 5-bromo-4-chloro-3-indolyl β-D-galactoside (XGal)-containing Luria-Bertani agar plates, the efficiency of enrichment was calculated by simply counting the number of each colony.

At first, conditions were used (sodium acetate/acetic acid buffer, pM 4.8–5.0) where efficient triplex formation between pTC45 and oligo- or poly(T–C)$_n$ was observed by simple gel electrophoretic assays (Lyamichev, V. I., Mirkin, S. M., Frank-Kamenetskii, M. D. & Cantor, C. R. (1988) *Nucleic Acids Res.* 16:2165–2178; Lee, J. S., Latimer, L. J. P., Haug, B. L., Pulleyblank, D. E., Skinner, D. M. & Burkholder, G. D. (1989) *Gene* 82:191–199; and our unpublished observations). However, no significant enrichment of white colonies (that is, pTC45) was obtained (data not shown). It is conceivable that this is due to nonspecific interaction between DNA and streptavidin on the beads, since streptavidin, with an estimated isoelectric point of 5–6 (Green, N. M. (1990) *Methods Enzymol.* 184:51–67), may well be positively charged under these conditions. To reduce such undesirable interactions, the ionic strength of the reaction buffer was increased by the addition of NaCl to final concentration of 2M. [This would also increase the thermal stability of the triple helix (Plum, C. E., Park, Y. -W., Singleton, S. F., Dervan, P. B. Breslauer, K. J. (1990) *Proc. Natl. Acad. Sci. USA* 87:9463–9467).] A very efficient enrichment, calculated to be 1.8×10$^5$-fold with a recovery of ≈80%, was obtained with the use of this modified buffer (see Table 1, for example). White colonies, that had accounted for 0.5% of the total colonies in the original library, were routinely enriched to account for more than 95% of the resultant library after a single round of the procedure. Occasionally, no blue colonies at all were observed. A slightly higher efficiency was reproducibly obtained when linearized plasmids were used rather than circular ones (data not shown). Thus, the use of linearized plasmids is recommended to obtain the highest efficiency purification, although this requires the additional steps of enzyme digestion before triplex formation and self-circularization before bacterial transformation.

TABLE 1

Triplex-mediated enrichment of target plasmids from a reconstituted library

| Colonies, no. (%) | |
|---|---|
| White (pTC45) | Blue (pUC19) |
| Before enrichment | |
| $5.0 \times 10^4$ (0.5) | $1.1 \times 10^7$ (99.5) |
| After enrichment | |
| $4.0 \times 10^4$ (99.9) | $0.5 \times 10^2$ (0.1) |

The effects of various parameters on triplex affinity capture could be followed also by simple gel electrophoresis. For example, a mixture of linearized pTC45 and λ/BstEII fragments was subjected to the triplex affinity capture procedure at various pHs, and the recovered DNAs were electrophoresed on an agarose gel (see FIG. 2 Lanes: 1 and 8, input DNA; lanes 2–7, reactions at pH 4.5, 5.0, 5.5, 6.0, 6.5, and 7.0, respectively. The arrow indicates the position of pTC45). It should be noted that the 5.7-kilobase (kb) BstEII fragment derived from the left extremity of phage λ DNA, which does not contain any complete $(dT-dC)_n \cdot (dG-dA)_n$ sequences longer than 7 bp but does contain some interrupted ones, also bound weakly to BTC-20 (SEQ ID NO:1) under very acidic condition (pH 4.5 or less). Note that part of this fragment was recovered as a non-covalent complex, with the right arm fragment joined at the cos site (see FIG. 2, lane 2). Increasing the pH up to ~6.0 eliminated this weak binding without any significant reduction in recovery of pTC45 DNA (FIG. 2, lanes 3–5), whereas further increase in pH reduced the recovery considerably (FIG. 2, lanes 6 and 7). These results indicate that the stringency of the triplex affinity capture can be controlled simply by changing the pH. The same assay system also revealed the nonspecific interaction between DNA and the magnetic beads and its elimination by the high ionic strength buffer, confirming the result described above (data not shown).

Triplex Affinity Capture of $(dT-dC)_n \cdot (dG-dA)_n$ Dinucleotide Repeats from a Human Genomic Library After initial experiments with the model plasmid system, the procedure was applied to the isolation of $(dT-dC)_n \cdot (dG-dA)_n$ dinucleotide repeats from human genome. This sequence is a member of so-called "microsatellite" DNAs distributed throughout mammalian genomes (Manor, H., Rao, B. S. & Martin, G. R. (1988) *J. Mol. Evol.* 27:96–101; Wong, A. K. C., Yee, H. A., van de Sande, J. H. & Rattner, J. B. (1990) *Chromosoma* 99:344–351). It is often hypervariable in the number of the repeat units (a) from individual to individual and thus provides highly informative DNA markers for genetic linkage mapping (Tautz, D. (1989) *Nucleic Acids Res.* 17:6463–6471; Love, J. M., Knight, A. M., McAleen, M. A. & Todd, J. A. (1990) *Nucleic Acids Res.* 18:4123–4130; Moore, S. S., Sargeant, L. L., King, T. J., Mattick, J. S., Georges, M. & Hetzel, D. J. S. (1991) *Genomics* 10:654–660; Weber, J. L. (1990) in Genome Analysis, eds. Davies, K. E. & Tilghman, S. M. (Cold Spring Harbor Lab., Cold Spring Harbor, N.Y.). Vol. 1, pp. 159–181).

Plasmids prepared from a human chromosome 21-specific library were linearized by digestion at a unique HindIII site on each clone (Ito, T., Ohgusu, H., Oishi, N. & Sakaki, Y. (1991) *Genomics* 9:707–712) and subjected to the procedure described above. Eighteen randomly chosen clones were further analyzed. Plasmids from these clones were tested for triplex formation by binding assays similar to the one discussed above and shown in FIG. 2. All these clones were able to form triplexes with BTC-20 (SEQ ID NO:1) (data not shown).

These plasmids were then tested to determine whether or not they contained $(dT-dC)_n \cdot (dG-dA)_n$ sequences using a PCR-based method originally developed by Kunkel and coworkers (Feener, C. A., Boyce, F. M. & Kunkel, L. M. (1991) *Am. J. Hum. Genet.* 48:621–627). In this assay, a $(T-C)_n$ oligonucleotide and one of the sequencing primers were combined and used as PCR primers. If the tested insert contains a $(dT-dC)_n \cdot (dG-dA)_n$ sequence(s), amplified products should be obtained by, at least, one of the primer combinations depending on the relative orientation of the dinucleotide repeat. In practice, 17 clones of the 18 tested gave distinct PCR products, part of which are shown in FIG. 3. The results demonstrated that the triplex-mediated procedure is quite effective and useful for selection of $(dT-dC)_n \cdot (dG-dA)_n$ dinucleotide repeat clones and, thus, for the subsequent development of highly informative DNA markers for genetic linkage mapping. (FIG. 3 shows the results of the PCR-based assay for the $(dT-dc)_n \cdot (dG-dA)_n$ dinucleotide repeats on six of the eighteen randomly chosen clones (nos. 1–6) purified by TAC from a chromosome 21-specific library. PCR was performed with forward and reverse primers (each left lane), forward and BamTC (SEQ ID NO:2) primers (each middle lane), and reverse and BamTC (SEQ ID NO:2) primers (each right lane). Lanes M contain phage λ DNA digested with HindIII (outside) and BstEII (inside)).

Example 2

The TAC method of the invention is further demonstrated by isolating a single copy clone from a yeast genomic library.

Genomic DNA from a *Saccharomyces cerevisiae* strain containing a triplex-forming site integrated at the LEU2 locus (Strobel, S. A. and Dervan, P. B. (1991) *Nature* 310:172–174) was digested with BglII and cloned into the BamHI site of pTZ19RG vector, a variant of pTZ19RG containing rare-cutter sites. pTZ19RG is a derivative of pTZ19R (Pharmacia) bearing an additional 12 bp sequence (SEQ ID NO:3) between SphI and PstI sites in its multiple cloning site.

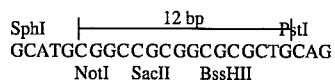

Accordingly, the vector newly obtained NotI, SacII and BssHII sites without losing original restriction sites in pTZ19R and the reading frame of the lacZ gene.

Plasmid DNA (~2 µg) from the library was isolated, digested with NotI and incubated with 10 pmol of 5'-biotinylated $CT_2CT_4CT_2CT_3CT_5CT_2$ (SEQ ID NO:4) in 2M NaCl, 0.1M sodium phosphate buffer (pH 6.0) for 2 hr at 50° C. Then, ~0.2 mg of streptavidin-coated magnetic beads (Dynal, Streptavidin M-280) were added, collected by a magnet after 1 hour of incubation and washed extensively with the same buffer. Captured DNAs were released by incubation in 1M Tris-HCl (pH 9), 0.5 mM EDTA for 20 min, recovered by ethanol precipitation, recircularized and used for transformation of competent DH5α cells as set forth in Example 1. Plasmid DNA isolated from the cultures was analyzed by gel electrophoresis as also set forth in Example 1. One purification cycle at pH 6.0 yielded an enriched library with a complex electrophoretic pattern, although some bands were significantly enriched compared to the original library. A second TAC cycle at more stringent condition (pH 6.2) provided a simple population composed of only four DNA species, named A-D according to their sizes. Analysis of twelve randomly chosen clones showed that they contained two A, six B, two C and two D. Restriction mapping and PCR using primers specific to the LEU2 locus of this strain showed that clone B was the desired target. Other clones (A, C and D) may be derived from pseudo-target sites in this strain, as suggested by previous affinity cleaving experiments (Strobel, S. A. and Dervan, P. B. (1991) Nature 310:172–174). An additional cycle of TAC where all steps were performed at 50° C. distinguished the target clone from the pseudo-clones, although the yield was low. Conditions for a single step purification of B from the total library were not identified.

Example 3

The method of the invention was also demonstrated using triple-affinity capture in combination with electrophoresis.

Materials and Methods

A biotinylated oligonucleotide BTC20 (5'-biotinylated $(TC)_{10}$) (SEQ ID NO:1) and plasmid DNAs, pUC19 and pTC45 were linearized by digestion with EcoRI and incubated in 0.2M sodium acetate buffer (pH 4.86) at 50° C. as described in Example 1. The mixture was electrophoresed in an agarose gel (0.8%, LE agarose, FMC) in 1M sodium acetate buffer (pH 4.86) equipped with a streptavidin trap. Streptavidin M-280, Dynal). The trap was made by allowing a suspension (~5 mg/ml final concentration) of streptavidin-coated magnetic beads (Dynabeads Streptavidin M-280, Dynal) in 1% molten Inert Agarose (FMC) to solidify in a second well (1 mm thick) in front of the origin well. Electrophoresis was carried out in a cold room (4° C.) to avoid excess heating. In triplex affinity capture electrophoresis, target DNA was complexed with the biotinylated pyrimidine-rich oligonucleotide probe by the spontaneous formation of a intermolecular triplex under acidic conditions. These intermolecular triplexes are quite stable during electrophoresis under acidic conditions (Lyamichev, V. I., Mirkin, S. M., Frank-Kamenetskii, M. D., Cantor, C. R. (1988) Nucleic Acids Res. 16:2165–2178). After electrophoresis, triplex DNA caught in the streptavidin trap was released by treatment with mild alkaline conditions. This treatment destabilized the triplex but not the Watson-Crick double helix so that the target DNA molecule was released in double-stranded form. Since oligonucleotide-directed triplex formation in agarose blocks was demonstrated previously (Strobel, S. A., Dervan, P. B. (1990) Science 249:73–75), all of these steps can be performed in agarose. As shown in Example 1, under mildly acidic conditions the plasmid pTC45 forms an intermolecular triplex with BTC20, whereas the former does not. Following incubation in the acidic buffer, each incubation mixture was electrophoreses in a high ionic strength buffer through a gel equipped with a streptavidin trap. (See, FIG. 4; pTC45 (lanes 2 and 4); pUC19 (lanes 1 and 3.) This high-ionic strength buffer was used to minimize non-specific interaction between DNA and streptavidin at acidic pH as discussed in Example 1. As shown in FIG. 4, plasmid pTC45 was (compare lanes 2 & 4) almost completely captured by the trap, whereas plasmid pUC19 passed through the trap without any significant entrapment or retardation (compare lanes 1 & 3). The captured DNA could be released by incubating the trap in mild alkaline buffer.

Example 4

The affinity capture electrophoresis method of the invention is further demonstrated using a poly-dU-tailed oligonucleotide to bind to a poly-dA-tailed target DNA and electrophoresing the subsequent complex in a gel equipped with a solid phase trap.

Plasmid pUC19, linearized by digestion with Sac I and tailed with dATP using terminal deoxynucleotidyl transferase, was mixed with λ/Hind III fragments. Separately, a biotinylated oligonucleotide BTC20 (SEQ ID NO:1) was tailed with dUTP. Both were mixed and incubated in TE buffer (Sambrook, J., Fritsch E. F., Maniatis, T., Molecular Cloning, A Laboratory Manual, 2nd Ed., Cold Spring Harbor, Cold Spring Harbor Press, 1989) containing 0.5M NaCl at 68° C. for 15 min and stored at room temperature until use. The mixture was diluted to 0.1M NaCl/TE and loaded onto a 1% agarose gel equipped with a streptavidin trap in TBE buffer (Sambrook, J., Fritsch E. F., Maniatis, T., Molecular Cloning, A Laboratory Manual, 2nd Ed., Cold Spring Harbor, Cold Spring Harbor Press, 1989). (See FIG. 5. Lane 1 was equipped with a mock trap, lane 2 with the streptavidin trap and lane 3 contains the starting mixture run as the control.) After the run, the trap was removed from the gel before staining with ethidium bromide. The trap was incubated in 100–200 μl of TBE buffer containing 5 units of uracil N-glycosylase (UNG; Perkin Elmer Cetus) at 37° C. for 1 hr, and subjected to a second gel electrophoresis (see FIG. 5, lane 4).

The target, pUC19/Sac I fragment, but not the λ/Hind III fragments, was efficiently captured by the trap (FIG. 5, lanes 1 & 2). The trap was subsequently incubated in TBE buffer containing uracil N-glycosylase and subjected to a second electrophoresis. As shown in FIG. 5 (lane 4), the target fragment was released from the trap, proving its selective isolation. Exonucleases (T7 Gene 6 exonuclease or λ exonuclease) were also used to generate single-stranded ends which could be hybridized with the corresponding probes (data not shown). Although the intactness of both ends of the fragment is somewhat impaired, this method will be useful, in particular, when combined with linking clones (Smith, C. L., Warburton, P. E., Gaal, G. A., Gantor, C. R. (1986) In Setlow, J. K., Hollander, A. (eds), Genetic Engineering 8, New York, Plenum, 45–70). Furthermore, it might be applied to the selective capture of telomeric DNA fragments using the single-stranded portion of the telomere repeats as the targets for hybridization.

Trapping efficiency appeared to be almost complete in both the ACE method used in Example 3 and this Example since no untrapped targets were observed at expected positions after the traps (FIGS. 4 and 5). Furthermore, in the case of end affinity capture electrophoresis, the target fragment was recovered without visible contaminating non-target DNA (FIG. 5), although recoveries appear to be somewhat lower than with the triplex affinity capture method. The reduced recovery may be due to diffusion of DNAs from the trap during the incubation with UNG.

All publications mentioned in this specification are herein incorporated by reference to the same extent as if each individual publication or patent application was specifically and individually indicated to be incorporated by reference.

What is claimed is:

1. A method for purifying intact a particular double stranded DNA present in a sample comprising the steps of:

(a) contacting the sample with an oligonucleotide coupled either directly or indirectly to a first recognition molecule of a specific molecular recognition system to form a triple-helix between the particular double stranded DNA and the coupled oligonucleotide, said oligonucleotide being an oligodeoxyribonucleotide or an oligoribonucleotide;

(b) contacting the reaction medium obtained in step (a) with a solid carrier to which is either directly or indirectly fixed a second recognition molecule of the molecular recognition system, the second recognition molecule specifically binding to the first recognition molecule;

(c) separating the reaction medium from the solid phase in step (b);

(d) separating the particular double stranded DNA from the oligonucleotide by treating the separated solid phase of step (c) with an alkaline reagent that breaks the bonds between the oligonucleotide and the particular double stranded DNA but conserves the double strandedness of the particular double stranded DNA, said reagent having a pH that is about 8.0 to about 10.0 if said oligonucleotide is an oligodeoxyribonucleotide or a pH that is no greater than about: 8.5 if said oligonucleotide is an oligoribonucleotide; and (e) recovering the particular double stranded DNA.

2. The method of claim 1 wherein the double stranded DNA comprises a plasmid DNA.

3. The method of claim 2 wherein the plasmid DNA is a single copy clone from a yeast genomic library.

4. The method of claim 1 wherein the double stranded DNA comprises a lambda DNA.

5. The method of claim 1 wherein the oligonucleotide is a pyrimidine rich oligonucleotide.

6. The method of claim 5 wherein the oligonucleotide comprises a homopyrimidine oligonucleotide.

7. The method of claim 6 wherein the homopyrimidine is biotinylated at the 5' end.

8. The method of claim 7 wherein the homopyrimidine comprises 5'-biotinylated $CT_2CT_4CT_2CT_3CT_5CT_2$.

9. The method of claim 7 wherein the homopyrimidine comprises 5'-biotinylated $(T-C)_{10}$.

10. The method of claim 1 wherein the oligonucleotide includes the sequence $(T-C)_n$ where n is at least 4.

11. The method of claim 1 wherein the oligonucleotide comprises a purine rich nucleotide.

12. The method of claim 1 wherein the molecular recognition system is selected from the group consisting of an antigen/antibody, an avidin/biotin, a streptavidin/biotin, a protein A/Ig and a lectin/carbohydrate system.

13. The method of claim 12 wherein the molecular recognition system comprises an antigen/antibody system wherein the antigen is digoxigenin and the antibody is anti-digoxigenin antibody.

14. The method of claim 1 wherein the solid carrier is selected from a group consisting of particles, beads or a porous matrix.

15. The method of claim 1 wherein the solid carrier is selected from a group consisting of a plastic, glass, agarose, cellulose, nitrocellulose, nylon, silicon or metal solid carrier.

16. The method of claim 1 wherein the solid carrier fixed with a second recognition molecule comprises streptavidin coated beads.

17. The method of claim 12 wherein the molecular recognition system comprises a streptavidin/biotin system, the coupled oligonucleotide comprises a biotinylated homopyrimidine and the solid carrier to which is fixed a second recognition molecule comprises a streptavidin coated magnetic solid phase.

18. A method for purifying intact a particular double stranded DNA in a sample comprising the steps of:

(a) contacting the sample with a biotinylated oligonucleotide under acidic conditions to form by means of Hoogsteen hydrogen bonding, a triple-helix between the particular DNA and the oligonucleotide, said oligonucleotide being an oligodeoxyribonucleotide or an oligoribonucleotide;

(b) contacting the reaction medium obtained in step (a) with streptavidin coated magnetic beads to indirectly attach the triple-helix to the magnetic beads by means of biotin/streptavidin binding;

(c) separating the reaction medium from the magnetic beads;

(d) separating the particular double-stranded DNA from the oligonucleotide by incubating the magnetic beads of step (c) with a basic buffer that destablizes the Hoogsteen hydrogen bonds between the oligonucleotide and the particular double-stranded DNA but not the Watson-Crick bonds, said buffer having a pH that is about 8.0 to about 10.0 if said oligonucleotide is an oliogodeoxyribonucleotide or a pH that is no greater than about 8.5, if said oligonucleotide is an oligoribonucleotide; and (e) recovering the particular double stranded DNA from step (d).

19. A method for the determination of a particular double stranded DNA in a sample comprising the steps of:

(a) contacting the sample with an oligonucleotide coupled either directly or indirectly to a first recognition molecule of a specific molecular recognition system to form a triple-helix between the particular double stranded DNA and the coupled oligonucleotide, said oligonucleotide being an oligodeoxyribonucleotide or an oligoribonucleotide and said particular DNA remaining intact during triple helix formation;

(b) contacting the reaction medium obtained in step (a) with a solid carrier to which is either directly or indirectly fixed a second recognition molecule of the molecular recognition system, the second recognition molecule specifically binding to the first recognition molecule;

(c) separating the reaction medium from the solid phase in step (b);

(d) separating intact the particular double stranded DNA from the oligonucleotide by treating the separated solid phase of step (c) with an alkaline reagent that breaks the bonds between the oligonucleotide and the particular double stranded DNA but conserves the double strandedness of the particular double stranded DNA, said reagent having a pH that is about 8.0 to about 10.0 if said oligonucleotide is an oligodeoxyribonucleotide or a pH that is no greater than about 8.5 if said oligonucleotide is an oligoribonucleotide;

(e) determining the DNA content of the eluate in step (d); and (f) relating the determination of step (e) to a standard to determine the specificity of the particular double stranded DNA in the sample.

20. A method for isolating intact a particular double stranded DNA in a sample comprising the steps of:

(a) incubating a sample containing the DNA with an oligonucleotide for a time sufficient for the oligonucleotide to form a triple helix with the particular DNA, said oligonucleotide being coupled either directly or indirectly to a first recognition molecule of a specific molecular recognition system, wherein said oligonucleotide is an oligodeoxyribonucleotide or an oligoribonucleotide;

(b) electrophoresing the reaction mixture obtained in step (a) in a gel containing a gel embedded solid carrier to which is either directly or indirectly fixed a second recognition molecule of the molecular recognition system, the second recognition molecule specifically binding to the first recognition molecule in the reaction mixture during electrophoresis;

(c) separating the solid phase in step (b) from the gel following electrophoresis;

(d) separating the particular double stranded DNA from the solid phase by treating the solid phase from (c) with a reagent that breaks the bonds between the DNA and the oligonucleotide but conserves the double strandedness of the particular double stranded DNA, said reagent having a pH that is about 8.0 to about 10.0 if said oligonucleotide is an oligodeoxyribonucleotide or a pH that is no greater than about 8.5 if said oligonucleotide is an oligoribonucleotide; and (e) recovering the particular double stranded DNA intact.

21. The method of claim 20 wherein the oligonucleotide coupled to a first recognition molecule comprises a biotinylated homopyrimidine oligodeoxyribonucleotide and the solid phase to which is fixed a second recognition molecule comprises streptavidin coated beads.

22. A method for isolating intact a particular double stranded DNA in a sample comprising the steps of:

(a) incubating a sample containing the particular DNA with a biotinylated homopyrimidine under acidic conditions to form by means of Hoogsteen hydrogen bonding a triple-helix between the DNA and the homopyrimidine, said homopyrimidine being an oligodeoxyribonucleotide or an oligoribonucleotide;

(b) electrophoresing the reaction mixture obtained in step (a) under acidic conditions in a gel containing a trap comprising immobilized streptavidin coated beads embedded in said gel, whereby the biotin coupled to the oligonucleotide-DNA triple-helix of step (a) binds to the streptavidin coated beads during electrophoresis;

(c) separating the resulting solid phase in step (b) from the gel following electrophoresis;

(d) separating the particular double stranded DNA from the solid phase by treating the solid phase from (c) with a basic buffer to break the Hoogsteen hydrogen bonds between the DNA and the oligonucleotide but not the Watson-Crick bonds between the double-stranded DNA, said buffer having a pH that is about 8.0 to about 10.0 if said homopyrimidine is an oligodeoxyribonucleotide or a pH that is no greater than about 8.5 if said homopyrimidine is an oligoribonucleotide; and (e) recovering the particular double stranded DNA intact.

23. A method for determination of a particular double stranded DNA in a sample comprising the steps of:

(a) incubating a sample with an oligonucleotide for a time sufficient for the oligonucleotide to form a triple helix with the particular DNA intact, said oligonucleotide being coupled either directly or indirectly to a first recognition molecule of a specific molecular recognition system, wherein said oligonucleotide is an oligodeoxyribonucleotide or an oligoribonucleotide;

(b) electrophoresing the reaction mixture obtained in step (a) in a gel containing a gel embedded solid carrier to which is either directly or indirectly fixed a second recognition molecule of the molecular recognition system under conditions for a time sufficient for the second recognition molecule to specifically bind to a first recognition molecule in the reaction mixture during electrophoresis;

(c) separating the solid phase in step (b) from the gel following electrophoresis;

(d) separating the particular DNA intact from the solid phase by treating the solid phase from (c) with a reaction medium that breaks the bonds between the DNA and the oligonucleotide, said medium having a pH that is about 8.0 to about 10.0 if said oligonucleotide is an oligodeoxyribonucleotide or a pH that is no greater than about 8.5 if said oligonucleotide is an oligoribonucleotide;

(e) determining the DNA content of the eluate in step (d); and (f) relating the determination of step (e) to a standard to determine the specificity of the DNA in the sample.

24. A method for purifying intact a particular double stranded DNA in a sample comprising the steps of:
   (a) contacting the sample with an oligonucleotide coupled either directly or indirectly to a first recognition molecule of a specific molecular recognition system and with a solid carrier to which is either directly or indirectly fixed a second recognition molecule of the molecular recognition system under conditions and for a time sufficient for the second recognition molecule to specifically bind to the first recognition molecule and for the coupled oligonucleotide and the DNA to form a triple helix, said oligonucleotide being an oligodeoxyribonucleotide or an oligoribonucleotide;
   (b) separating the reaction medium from the solid phase in step (a);
   (c) separating the particular double stranded DNA from the oligonucleotide by treating the separated solid phase of step (b) with an alkaline reagent that breaks the bonds between the oligonucleotide and the particular double stranded DNA but conserves the double strandednes of the particular double stranded DNA, said reagent having a pH that is about 8.0 to about 10.0 if said oligonucleotide is an oligodeoxyribonucleotide or a pH that is no greater than about 8.5 if said oligonucleotide is an oligoribonucleotide; and
   (d) recovering intact the particular double stranded DNA.

25. A method for purifying intact a particular double stranded DNA in a sample comprising the steps of:
   (a) contacting the sample with a specific oligonucleotide backbone analog coupled either directly or indirectly to a first recognition molecule of a specific molecular recognition system to form a triple-helix between the particular DNA and the coupled oligonucleotide analog, said oligonucleotide being an oligodeoxyribonucleotide or an oligoribonucleotide;
   (b) contacting the reaction medium obtained in step (a) with a solid carrier to which is either directly or indirectly fixed a second recognition molecule of the molecular recognition system, the second recognition molecule specifically binding to the first recognition molecule;
   (c) separating the reaction medium from the solid phase in step (b);
   (d) separating the particular double stranded DNA from the oligonucleotide analog by treating the separated solid phase of step (c) with a reagent that breaks the bonds between the oligonucleotide backbone analog and the particular DNA but conserves the double strandedness of the particular double stranded DNA, said reagent having a pH that is about 8.0 to about 10.0 if said oligonucleotide is an oligodeoxyribonucleotide or a pH that is no greater than about 8.5 if said oligonucleotide is an oligoribonucleotide; and
   (e) recovering the particular double stranded DNA intact.

26. The method of claim 25 wherein the oligonucleotide backbone analog is selected from the group consisting of polyamide nucleic acids and phosphotriesters.

27. A method for purifying intact a particular double stranded DNA in a sample comprising the steps of:
   (a) forming an immobilized triple helix with the particular DNA by means of a biotinylated oligonucleotide and streptavidin coated beads, wherein said oligonucleotide is an oligodeoxyribonucleotide or an oligoribonucleotide;
   (b) separating the particular double stranded DNA from the triple helix in (a) by treating the triple helix with an alkaline reagent that breaks Hoogsteen hydrogen triplex bonds but not Watson-Crick hydrogen duplex bonds, said reagent having a pH that is about 8.0 to about 10.0 if said oligonucleotide is an oligodeoxyribonucleotide or a pH that is no greater than about 8.5 if said oligonucleotide is an oligoribonucleotide; and
   (c) recovering the particular double stranded DNA intact.

* * * * *

UNITED STATES PATENT AND TRADEMARK OFFICE
CERTIFICATE OF CORRECTION

PATENT NO. : 5,482,836
DATED : January 9, 1996
INVENTOR(S) : Cantor, et al

It is certified that error appears in the above-indentified patent and that said Letters Patent is hereby corrected as shown below:

On Cover page, in [56], under OTHER PUBLICATIONS, line 8, delete "9cover" and insert therefore --(cover--.

Column 13, line 42, delete "HindIII" and insert therefor --*Hind*III--.

Column 15, line 25, delete "BstEII" and insert therefor --*Bst*EII--.

Column 15, line 67, delete "HindIII" and insert therefor --*Hind*III--.

Column 16, line 33, delete "HindIII" and insert therefor --*Hind*III--.

Column 16, line 33, delete "BstEII" and insert therefor --*Bst*EII--.

Column 16, line 41, delete "LEU2" and insert therefor --*LEU2*--.

Column 16, line 43, delete "BglII" and insert therefor --*Bgl*II--.

Column 16, line 59, delete "NotI" and insert therefor --*Not*I--.

Column 17, line 13, delete "LEU2" and insert therefor --LEU2--.

Column 17, line 43, immediately preceding "In" insert --[new paragraph]--.

UNITED STATES PATENT AND TRADEMARK OFFICE
CERTIFICATE OF CORRECTION

PATENT NO. : 5,482,836  Page 2 of 2
DATED : January 9, 1996
INVENTOR(S) : Cantor et al.

It is certified that error appears in the above-indentified patent and that said Letters Patent is hereby corrected as shown below:

Column 18, line 16, delete "Hind III" should insert therefor --Hind III--

Column 18, line 35, delete "$Sac\ I$ and insert therefor --*Sac* I--.

Column 18, line 35, delete "Hind III" and insert therefor --*Hind* III--.

Claim 1, column 21, line 49, immediately following "about" delete --:--.

Claim 8, column 21, line 65, immediately following "$CT_2$," insert --(SEQ ID NO:4)--.

Claim 9, column 21, line 67, immediately following "$(T-C)_{10}$" insert --(SEQ ID NO:1)--.

Claim 20, column 23, line 54, delete "(a)in" and insert therefor --(a) in--.

Claim 23, column 24, line 48, delete "(a)in" and insert therefor --(a) in--.

Signed and Sealed this

Twenty-fifth Day of June, 1996

BRUCE LEHMAN

*Attest:*

*Attesting Officer*    *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note="BTC-20 Oligonucleotide, biotinylated at 5'-end."

( x i ) SEQUENCE DESCRIPTION: SEQ ID NO:1:

TCTCTCTCTC TCTCTCTCTC         20

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..27
        ( D ) OTHER INFORMATION: /note="BamTC oligonucleotide."

( x i ) SEQUENCE DESCRIPTION: SEQ ID NO:2:

CCCGGATCCT CTCTCTCTCT CTCTCTC         27

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note="SphI restriction site."

( i x ) FEATURE:
        ( A ) NAME/KEY: misc_feature
        ( B ) LOCATION: 19..24
        ( D ) OTHER INFORMATION: /note="PstI restriction site."

( i x ) FEATURE:
        ( A ) NAME/KEY: misc_feature
        ( B ) LOCATION: 6..19
        ( D ) OTHER INFORMATION: /note="The 12 bp sequence between -continued SphI and PstI restriction sites contains NotI,
SacII and BssII restriction sites."

(xi) SEQUENCE DESCRIPTION: SEQ ID NO:3:

GCATGCGGCC GCGGCGCGCT GCAG                        24

(2) INFORMATION FOR SEQ ID NO:4:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

CTTCTTTTCT TCTTTCTTTT TCTT                        24